United States Patent [19]
Tornier et al.

[11] Patent Number: 5,662,651
[45] Date of Patent: Sep. 2, 1997

[54] EXTERNAL OR INTERNAL FIXATOR FOR REPAIRING FRACTURES OR ARTHROPLASTIES OF THE SKELETON

[75] Inventors: Alain Tornier, Saint-Ismier, France; Patrick Kluger, Erbach, Germany

[73] Assignee: Tornier S.A., Saint-Ismier, France

[21] Appl. No.: 523,760

[22] Filed: Sep. 5, 1995

[30] Foreign Application Priority Data

Sep. 15, 1994 [FR] France ................................. 94 11224

[51] Int. Cl.[6] ................................................ A61B 17/68
[52] U.S. Cl. ........................ 606/60; 606/61; 606/72; 606/54
[58] Field of Search ........................ 606/60, 61, 64, 606/66, 72, 73, 54

[56] References Cited

U.S. PATENT DOCUMENTS 4,987,892  1/1991  Krag et al. .
5,002,542  3/1991  Frigg .
5,344,422  9/1994  Frigg .
5,382,248  1/1995  Jacobson et al. ........................ 606/60

FOREIGN PATENT DOCUMENTS

WO9401049  1/1994  WIPO .

Primary Examiner—Michael Buiz
Assistant Examiner—Daphna Shai
Attorney, Agent, or Firm—Dowell & Dowell

[57] ABSTRACT

A skeletal fixator including implant screws, a support angularly indexed with respect to a head of the implant screws and which comprises a cavity provided with a screw thread adapted to receive a connecting rod having a screw thread of pitch different from that of the thread of the cavity. A locking screw cooperates with the head of the implant screw to clamp and bind the connecting rod relative to the implant screws.

9 Claims, 3 Drawing Sheets 5,662,651

EXTERNAL OR INTERNAL FIXATOR FOR REPAIRING FRACTURES OR ARTHROPLASTIES OF THE SKELETON

FIELD OF THE INVENTION

The present invention relates to an external or internal fixator intended for repairing the skeleton in the event of fractures or arthroplasties. The fixator according to the invention may for example be used in spine-repair surgery.

BACKGROUND OF THE INVENTION

In orthopedics, fixators, whether they be internal or external, generally comprise screws which are implanted in the bones to be assembled or joined, and which are connected together by a rigid system such as a connecting rod. The function of fixators of this type is to maintain a relative position of each fragment of bone to obtain the stability necessary for consolidation of the fracture or of the arthroplasty.

The principal difficulties of this type of fixator concern the rigidity of the assembly which is not sufficient to maintain the position of repair over time and to ensure a perfect blockage in rotation and in translation of the connecting rods.

It is a more particular object of the present invention to overcome these drawbacks.

SUMMARY OF THE INVENTION

The fixator according to the present invention comprises on each screw previously implanted in the bone, a support angularly orient able with respect to the head of such screw and which comprises a cavity in the form of a portion of circle of which the bottom is provided with a thread adapted to receive a connecting rod. The connecting rod is a thread of pitch different from that of the cavity, while another screw cooperates with the head of each screw implanted in the bone to allow immobilization, on the one hand, of the support in rotation about the head and, on the other hand, of the threaded rod in rotation and in translation about its axis.

BRIEF DESCRIPTION OF THE DRAWINGS

The invention will be more readily understood on reading the following description with reference to the accompanying drawings, in which.

DESCRIPTION OF PREFERRED EMBODIMENT

Figure 1:
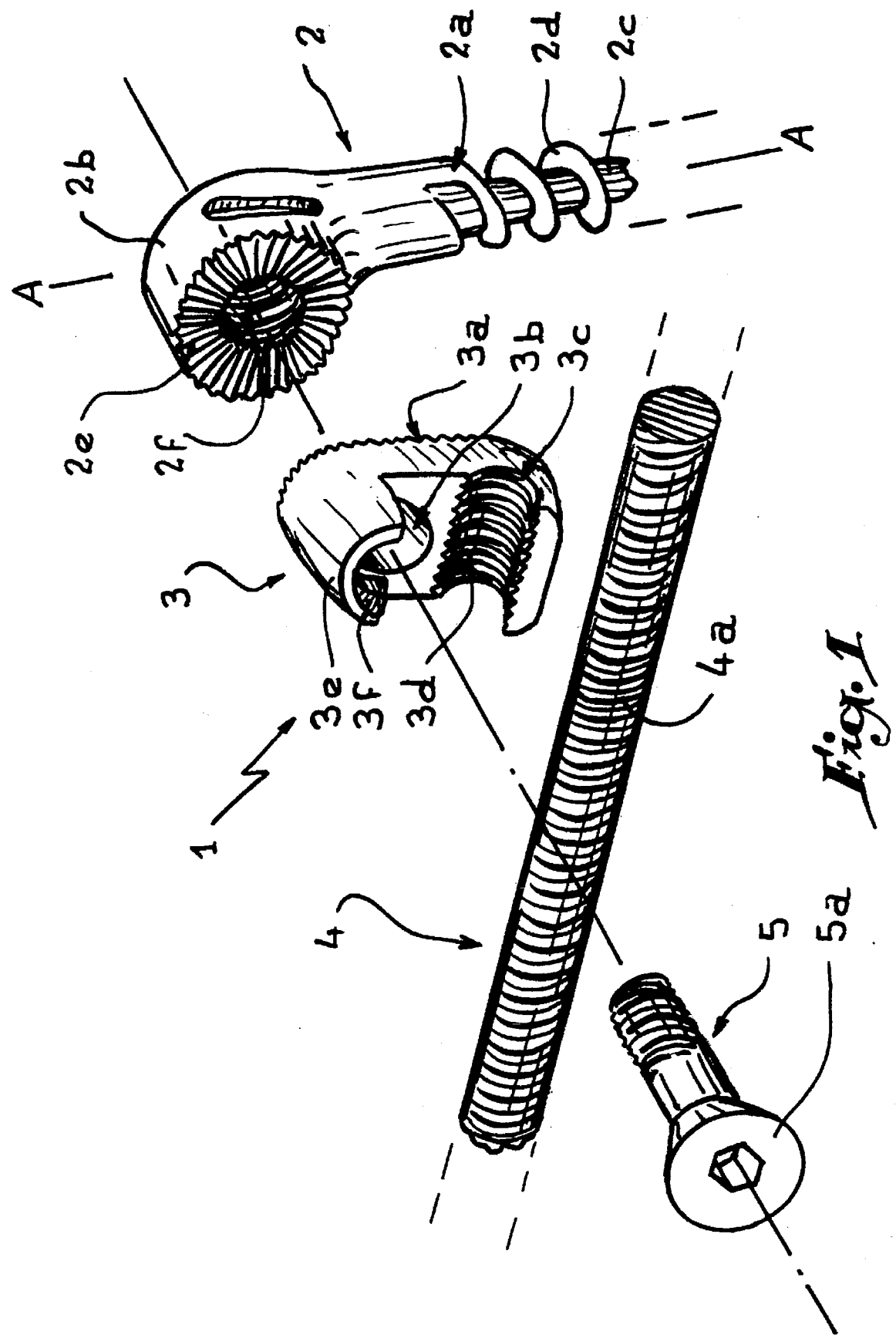
FIG. 1 is a perspective assembly view illustrating the different elements comprising the fixator according to the invention.
Figure 2:
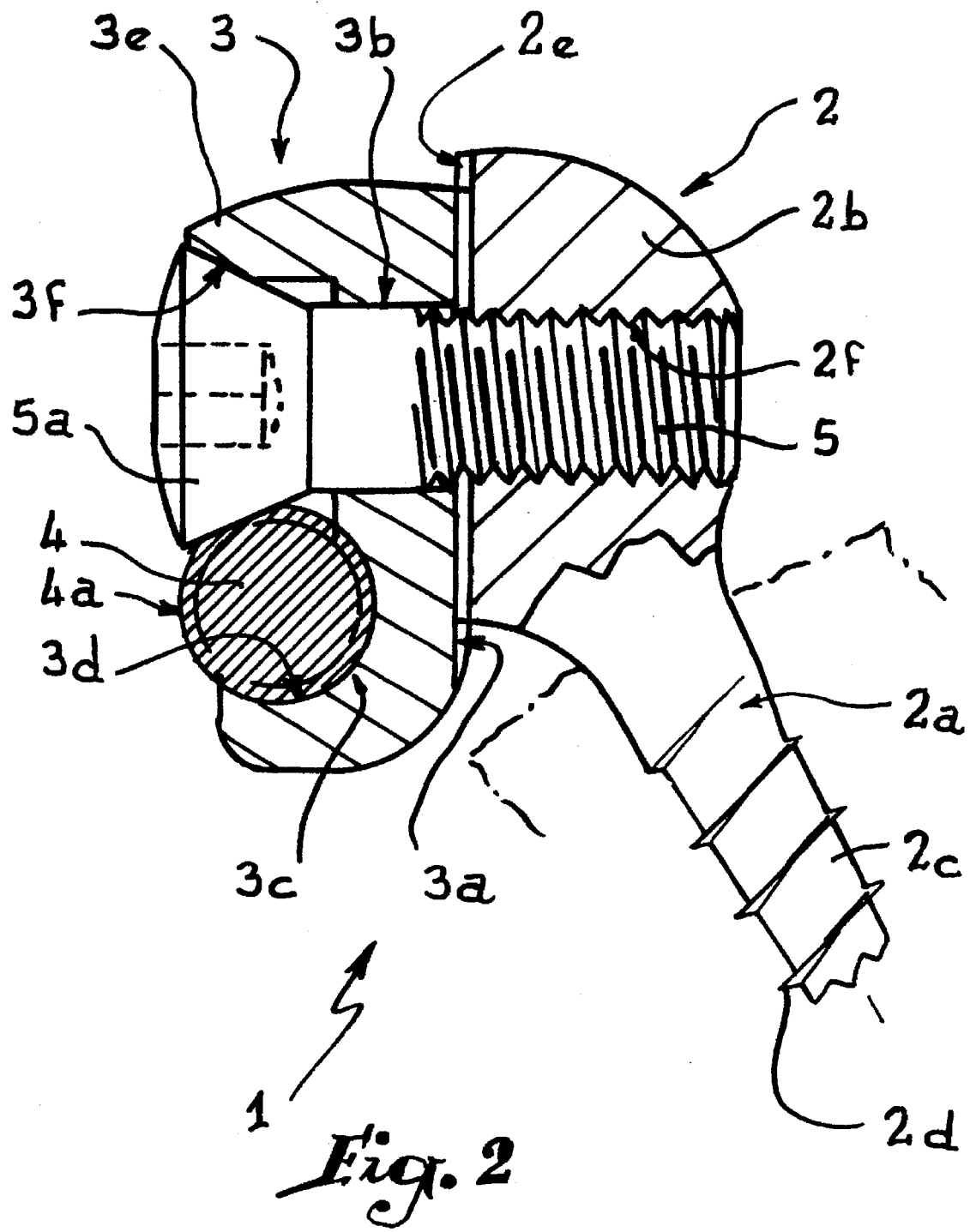
FIG. 2 is a section showing the fixator in mounted position.

Referring now to the drawings, FIGS. 1 and 2 show an external or internal fixator 1 comprising on each screw 2 previously implanted in a bone, a support jaw 3 and a locking screw 5, which allow a connecting rod 4 to be axially retained.

Each screw 2 constituting the fixator 1 comprises a threaded part 2a and a spherical head 2b. The threaded part 2a presents a conical core 2c of equal resistance and a sharp-edged thread 2d. Thread 2d is provided to be of conical profile and sharp-edged over all or part of its length, or straight and sharp-edged over all or part of its length, or straight and sharp-edged over the length of part 2a.

The spherical head 2b of screw 2 comprises a notched face 2e which is disposed in a plane parallel to that of the vertical axis of the screw. The spherical head 2b includes at the centre of the notched face 2e and perpendicularly thereto with a tapped hole 2f.

The notched face 2e may be inclined with respect to the vertical axis of the screw by an angle of about 30° to 45°.

Each support 3 comprises a notched face 3a which comes into abutment against that, 2e, of the corresponding screw 2, allowing on the one hand, an angular indexation of the support and, on the other hand, the retaining in rotation thereof with respect to the head 2b of said screw. The support 3 has an open hole 3b coaxial to that, 2f, for the passage of screw 5 during tightening of the support on the head 2b of screw 2.

Opposite face 3a and at right angles with respect to the hole 3b, there is provided a cylindrical cavity 3c whose transverse section is in the form of a portion of circle. The bottom of the cavity 3c is, over the whole of its surface, provided with a thread 3d. Thread 3d may be provided over the whole length of the cavity 3c or only over a part thereof.

Opposite the cavity 3c and near the hole 3b, a skirt 3e in the form of a portion of circle is upstanding, provided in its end part with an inclined surface 3f directed towards the hole.

The threaded rod 4 connecting each screw 2 of the fixator 1 comprises a thread 4a whose pitch is slightly different from that of the thread 3d provided in the cavity 3c. When the fixator is assembled, it will be readily understood that the locking screw 5 allows immobilization of the support 3 and of rod 4 on the corresponding screw 2 of the fixator 1. In fact, the head 5a of the screw 5 abuts against the skirt 3e and the threaded rod 4 in order to block, on the one hand, the support 3 about the head 2b of the corresponding screw from rotating, after angular adjustment thereof, and, on the other hand, the threaded rod 4 from rotating and in translation by wedging of the threads 3d and 4a by reason of their different pitches (FIG. 2).

Of course, before fixing the support 3 and rod 4, the surgeon proceeds with positioning screws 2 on the fragments of bone to be joined. This type of fixator may be provided for example to join vertebrae of a spine in order to produce a fusion thereof.

Figure 3:
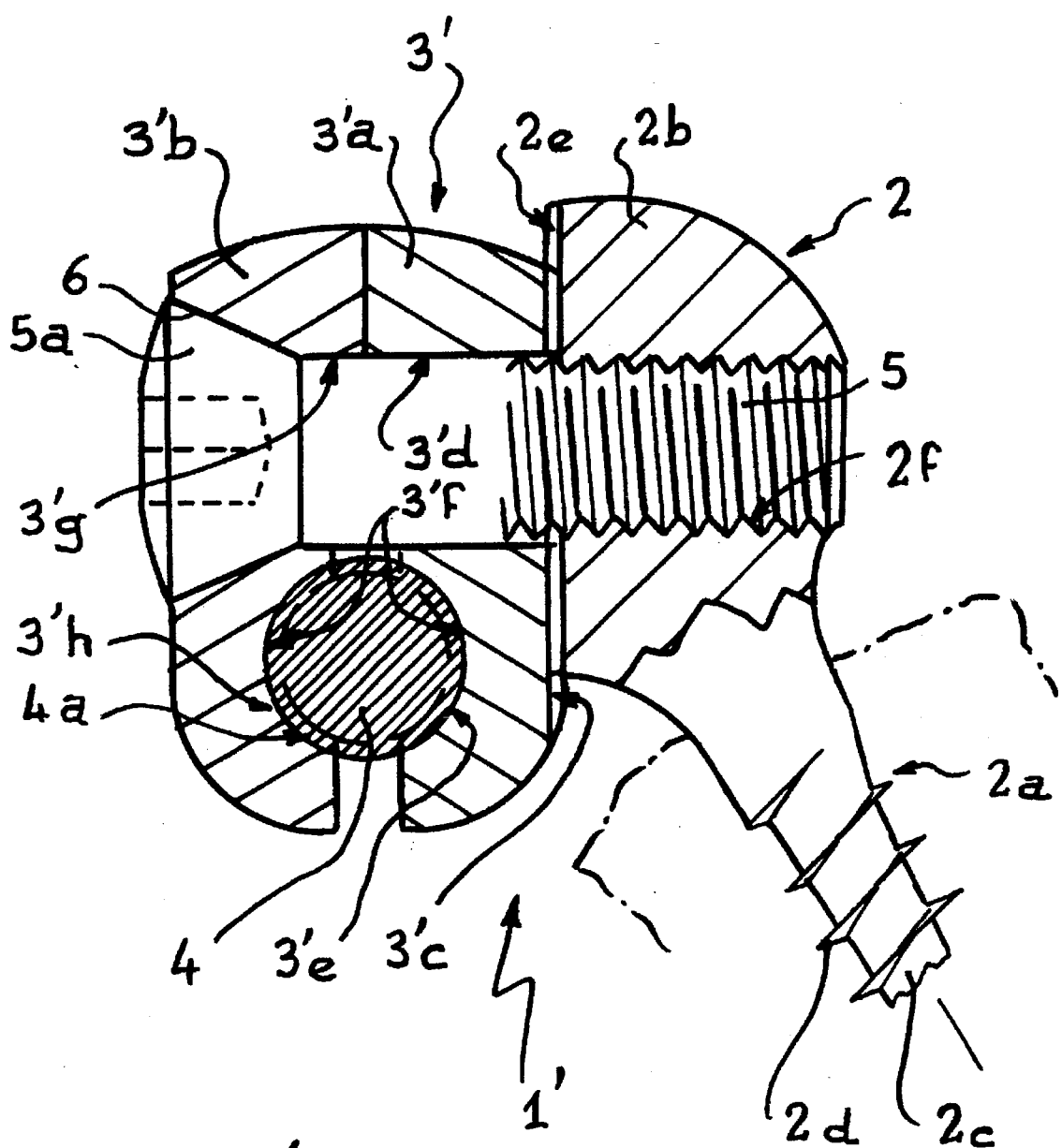
FIG. 3 is a section showing a variant of the fixator according to the invention.

FIG. 3 shows a variant embodiment of the fixator illustrated in FIGS. 1 and 2. In FIG. 3, the elements corresponding to those of FIGS. 1 and 2 have been referenced by the same numerals and same indices.

Thus, fixator 1' comprises a plurality of screws 2 previously implanted in each bone or fragment of bone, while the threaded rod 4 is retained axially via a support 3' constituted by two jaws 3'a, 3'b which are fixed on each head 2b of screws 2 by means of the locking screw 5.

The first jaw 3'a comprises a notched face 3'c which cooperates with that, 2e, of the corresponding screw 2 for the angular indexation of the support 3' with respect to the axis of the head 2b. The notched face 3'c has a smooth opening hole 3'd coaxial to that, 2f, for the passage of the locking screw 5. Opposite the notched face 3'c and at right angles with respect to the hole 3'd, there is a cavity 3'e whose transverse section is in the form of a portion of circle. The bottom of the cavity 3'e is provided with a thread 3'f whose pitch is different from that, 4a, of the rod 4 to effect a blocking, as described hereinbefore for fixator 1.

The second jaw 3'b also comprises a bore 3'g coaxial to the hole 3'd and provided with a truncated recess 6 for receiving the milled head 5a of the locking screw 5. The jaw 3'b comprises a cavity 3'h located above that, 3'e and presenting the same characteristics as the latter, i.e. a thread 3'f.

When each support 3' is assembled on the head 2b of the corresponding screw 2 with the aid of the locking screw, it is ascertained that the latter allows, on the one hand, blocking of the support 3' from rotation about the head and, on the other hand, tightening of the jaws 3'a and 3'b on the rod 4 so that the thread 4a cooperates closely with the threads 3'f of each of the cavities 3'e and 3'h so as to retain rod 4 rotation and translation.

It is observed that the fixators 1 and 1', whether they be external or internal, allow a perfect blocking in translation and in rotation of the connecting rod 4 between two screws 2 previously implanted in fragments of bone of a fracture or an ostheosynthesis of the spine.

It must, moreover, be understood that the foregoing description has been given only by way of example and that it in no way limits the domain of the invention which would not be exceeded by replacing the details of execution described by any other equivalents.

What is claimed is:

1. A fixator for repairing a fractured bone or arthroplasty comprising, an implant screw having a head and an anchor portion adapted to be anchored in a bone or arthoplasty, said anchor portion extending along an axis, a tapped hole in said head oriented transversely with respect to said axis, a first support jaw member having a first face adapted to be indexed with respect to said head of said implant screw, and a second oppositely oriented face, a semi-cylindrical cavity in said second face which includes at least along a portion thereof screw threads having a first thread pitch, an opening through said first support jaw member adjacent said cavity, a connecting rod having a screw threaded outer surface defined by a second thread pitch which is different than said first thread pitch, said connecting rod being seated within said cavity of said first support jaw member so that the threaded outer surface thereof is intermeshed with said screw threads of said cavity of said first support jaw member, and a locking member extending through said opening in said first support jaw member and into said tapped hole of said implant screw for simultaneously anchoring said first support jaw member to said head of said implant screw and for forcing said connecting rod into said cavity of said first support jaw member to thereby prevent movement of said retention rod relative to said first support jaw member.

2. The fixator of claim 1 in which said head of said implant screw includes a face oriented transversely with respect to said tapped hole which includes a plurality of notches, said first face of said first support jaw member including a plurality of notches which are complimentary with said plurality of notches in said face of said implant screw.

3. The fixator of claim 2 wherein said first support jaw member includes an arcuate skirt extending from said second face thereof and which is spaced on an opposite side of said opening through said first support jaw member from said cavity therein, said skirt including a tapered portion and said locking screw including a head having a tapered surface for cooperatively and simultaneouly engaging said tapered portion of said skirt of said first support jaw member and said connecting rod.

4. The fixator of claim 2 wherein said locking screw includes a head portion, a second support jaw member having a first face oriented towards said head portion of said locking screw and a second face opposing said second face of said first support jaw member, said second jaw support member including a semi-cylindrical cavity, said connecting rod being cooperatively seated within each of said semi-cylindrical cavities of said first and second support jaw members and an opening in said second support jaw member through which said locking screw extends.

5. The fixator of claim 4 wherein said semi-cylindrical cavity of said second support jaw member has screw threads extending along at least a portion thereof which are oriented at a thread pitch which is different than the second thread pitch of said connecting rod.

6. The fixator of claim 4 wherein said opening through said second support jaw member includes a tapered recess, and said head of said locking screw is truncated so as to cooperatively seat within said recess.

7. The fixator of claim 1 wherein said locking screw includes a head portion, a second support jaw member having a first face oriented towards said head portion of said locking screw and a second face opposing said second face of said first support jaw member, said second jaw support member including a semi-cylindrical cavity, said connecting rod being cooperatively seated within each of said semi-cylindrical cavities of said first and second support jaw members and an opening in said second support jaw member through which said locking screw extends.

8. The fixator of claim 7 wherein said semi-cylindrical cavity of said second support jaw member has screw threads extending along at least a portion thereof which are oriented at a thread pitch which is different than the second thread pitch of said connecting rod.

9. The fixator of claim 8 wherein said opening through said second support jaw member includes a tapered recess, and said head of said locking screw is truncated so as to cooperatively seat within said recess.

* * * * *